(12) United States Patent
Safarevich et al.

(10) Patent No.: US 6,293,594 B1
(45) Date of Patent: Sep. 25, 2001

(54) JOINING A WINDING TO A CONNECTOR USING A TRANSITION RING

(75) Inventors: Sergey Safarevich, Valencia; Benedict Gomperez, North Hollywood, both of CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/233,763

(22) Filed: Jan. 20, 1999

(51) Int. Cl.⁷ .............................. A61N 1/05; F16L 13/02; H01R 4/02
(52) U.S. Cl. .................... 285/21.1; 174/84 R; 174/94 R; 228/189; 285/288.1; 439/874; 607/37
(58) Field of Search ............................. 285/21.1, 148.12, 285/288.1, 288.11; 174/84 R, 94 R; 439/790, 874; 607/119, 122, 123, 125–128, 37; 228/189

(56) References Cited

U.S. PATENT DOCUMENTS

| 260,580 | * | 7/1882 | Knight ............................ 285/148.12 |
| 1,390,596 | | 9/1921 | Thornton, Jr. . |
| 1,613,461 | * | 1/1927 | Johnson ........................... 285/148.12 |
| 1,745,180 | | 1/1930 | Mischler .............................. 439/874 |
| 1,883,094 | * | 10/1932 | Taylor ................................ 285/288.1 |
| 1,908,859 | | 5/1933 | O'Neill ............................ 439/874 X |
| 1,977,846 | | 10/1934 | Febrey ..................................... 29/148 |
| 2,137,097 | * | 11/1938 | Sateren ............................ 285/148.12 |
| 2,185,450 | * | 11/1940 | Wager ............................ 285/288.1 X |
| 2,211,173 | * | 8/1940 | Shaffer ........................... 285/288.1 X |
| 2,308,089 | * | 1/1943 | McClary ....................... 285/288.11 X |
| 2,878,461 | | 3/1959 | Friedmann et al. .................. 339/275 |
| 3,406,444 | * | 10/1968 | Parker et al. .................... 285/21.1 X |
| 3,439,941 | * | 4/1969 | Nicol ............................. 285/288.1 X |
| 3,623,968 | * | 11/1971 | Bohne ........................... 285/288.1 X |
| 3,656,092 | | 4/1972 | Swengel, Sr. et al. ............ 339/213 T |
| 3,676,575 | | 7/1972 | Weaver et al. ...................... 174/94 R |
| 3,704,901 | * | 12/1972 | Borner ............................ 285/148.12 |
| 3,961,814 | * | 6/1976 | Byrne et al. ......................... 285/21.1 |
| 4,161,952 | | 7/1979 | Kinney et al. ........................ 128/786 |
| 4,352,714 | | 10/1982 | Patterson et al. ..................... 156/626 |
| 4,360,031 | | 11/1982 | White ................................... 128/786 |
| 4,784,161 | | 11/1988 | Skalsky et al. ....................... 128/785 |
| 4,844,099 | | 7/1989 | Skalsky et al. ....................... 128/785 |
| 4,915,426 | * | 4/1990 | Skipper ............................. 285/288.1 |
| 4,917,106 | | 4/1990 | Olivier ................................. 128/785 |
| 4,953,564 | | 9/1990 | Berthelsen ........................... 128/784 |
| 4,966,565 | | 10/1990 | Dohi ..................................... 439/874 |

(List continued on next page.)

*Primary Examiner*—Lloyd A. Gall

(57) ABSTRACT

A technique for joining an elongated wound element and a mating connector of a body implantable lead assembly comprises the steps of causing an end portion of the wound element to abut against a first end of a transition component having similar mass and heat transmission characteristics. The wound element is a coil of wire and the transition component is a ring member, both of which have similar inner and outer diameters. Further, the wire has a nominal diameter and the ring member has a similar transverse dimension. A laser beam is targeted generally at the location at which the end portion of the wound element abuts against the first end of the transition component such that the energy delivered thereto is substantially balanced between the wound element and the transition element, thereby thermally fusing the wound element and the transition component. The wound element and the transition component may be fabricated of the same alloy or of dissimilar alloys. Thereafter, a second end of the transition component distant from the first end is caused to abut against an end portion of the mating connector and the second end of the transition component is thermally fused to the end portion of the mating connector. In another embodiment, the ring member has an annular flange adjacent the first end, the annular flange being reduced in diameter substantially to the outer diameter of the wound element and of the mating connector upon completion of the thermal fusing step.

4 Claims, 2 Drawing Sheets

U.S. PATENT DOCUMENTS

| | | | |
|---|---|---|---|
| 5,115,818 | 5/1992 | Holleman et al. | 128/784 |
| 5,259,395 | 11/1993 | Li | 607/131 |
| 5,385,578 | 1/1995 | Bush et al. | 607/122 |
| 5,489,294 | 2/1996 | McVenes et al. | 607/120 |
| 5,522,872 | 6/1996 | Hoff | 607/119 |
| 5,522,874 | 6/1996 | Gates | 607/127 |
| 5,522,875 | 6/1996 | Gates et al. | 607/127 |
| 5,569,883 | 10/1996 | Walter et al. | 174/84 R |
| 5,571,146 | 11/1996 | Jones et al. | 607/37 |
| 5,676,694 | 10/1997 | Boser et al. | 607/122 |
| 5,716,390 | 2/1998 | Li | 607/127 |
| 5,728,149 | 3/1998 | Laske et al. | 607/122 |
| 5,746,616 | 5/1998 | Mar | 439/245 |

\* cited by examiner

JOINING A WINDING TO A CONNECTOR USING A TRANSITION RING

FIELD OF THE INVENTION

The present invention relates generally to lead assemblies for connecting implantable medical devices with selected body tissue to be stimulated by such devices, and more particularly to techniques for providing a secure electrical and mechanical connection between wound elements, such as coil conductors, and mating parts such as electrodes, sensors and the like, employed within such lead assemblies.

BACKGROUND OF THE INVENTION

Although it will become evident to those skilled in the art that the present invention is applicable to a variety of implantable medical devices utilizing pulse generators to stimulate selected body tissue, the invention and its background will be described principally in the context of a specific example of such devices, namely, cardiac pacemakers for providing precisely controlled stimulation pulses to the heart. The appended claims are not intended to be limited, however, to any specific example or embodiment described herein.

Pacemaker leads form the electrical connection between the cardiac pacemaker pulse generator and the heart tissue which is to be stimulated. As is well known, the leads connecting such pacemakers with the heart may be used for pacing or for sensing electrical signals produced by the heart or for both pacing and sensing in which case a single lead serves as a bidirectional pulse transmission link between the pacemaker and the heart. An endocardial type lead, that is, a lead which is inserted into a vein and guided therethrough into a cavity of the heart, includes at its distal end an electrode designed to contact the endocardium, the tissue lining the inside of the heart. The lead further includes a proximal end having a connector pin adapted to be received by a mating socket in the pacemaker. A flexible, coiled or wound conductor surrounded by an insulating tube or sheath couples the connector pin at the proximal end with the electrode at the distal end.

The purpose of the invention is to improve the reliability and manufacturability of a laser weld joint between a multi-wire winding and a connector. To achieve this, the winding is welded to a ring as a subassembly. The winding could be welded to the ring circumferentially or using a spot weld technique. The subassembly is subsequently welded to the connector during lead assembly.

The common weld joint comprises a winding screwed onto a cylindrical connector. The very last wind, or terminal end of the winding, are positioned against the shoulder of the connector. The shoulder and the terminal end of the winding are welded together (see FIG. 1).

It is challenging for the designer to create optimal welds when no transition exists between the wire ends and the connector. A number of problems are typically associated with connections between wound elements. For example:

1. The geometry of the "shoulder" design of the connector is such that it allows a weld joint to be formed from an unequal amount of material from each part joined. When unequal amounts of material are used to form a weld joint, the strength of the resultant joint is not repeatable.
2. It is difficult to determine the position where the laser beam should be applied to provide the proper amount of energy to each part (i.e. the laser beam is positioned more on the connector than on the wire because the connector requires more energy than does the wire).
3. Current configurations require that the conductor coil be expanded onto the connector ring which increases the outer diameter of the conductor coil and the size of the finished product.
4. The strength of the weld is sensitive to the position of the wire ends with respect to the connector (gaps between components).
5. The design is expected to be welded on the production line during lead assembly. It is difficult to use as a subassembly which would allow for an efficient manufacturing flow.
6. Another problem associated with connections between wound elements and mating components in present day lead assemblies arises from the use of different alloys for the wound elements and mating components. Since dissimilar alloys have different melt temperatures and other thermal properties, such connections are difficult to weld. Moreover, as lead sizes decrease, problems of manufacturability arise. This is particularly true where crimping is employed to secure the wound component to a mating element.

During welding in a typical joining operation, a laser beam applies a specific amount of energy to both the wire and the connector. Because the wire has less mass than the connector, the wire accumulates heat very quickly and melts easily. The connector, which has more mass, "draws" the heat out of the weld area, and does not melt to the same extent as the wire. This makes it difficult to melt the required amount of metal to fuse components together. Because of a lack of melted metal from the connector, the wire "necks down" as it spreads over the connector. The "negative weld reinforcement" from a lack of melted material from the connector reduces the strength of weld joint.

Therefore, the connector requires more laser energy to melt than does the wire. To achieve a weld of optimal strength, the beam energy must be balanced between the connector and the wire. The proper beam targeting requires placement of the laser beam not equally on the joint such that more energy is on the shoulder side than on the wire. It is difficult for the line operator to target the laser beam on the joint properly and consistently.

When joining parts consisting of different materials, the difference in material thermal properties magnifies the energy balance problem. For example, platinum requires much more energy to melt than MP35N. To equally melt the components of a joint consisting of MP35N wire and a platinum connector, a larger portion of the energy provided will need to be transferred to the platinum part.

The connector design requires that the conductor coil is expanded onto the connector. It is placed onto the connector in order to hold the coil relative to a shoulder of the connector. This expansion increases the outer diameter of the conductor coil which ultimately increases the size of the finished product.

A weld joint is also very sensitive to the position of the wire ends with respect to the connector when the parts to be joined are of significantly different masses. At least two surfaces of the connectors, the underlying connector and the shoulder, are in contact with the wire. Because an unequal amount of energy needs to be applied to the parts, the relative position of the parts affects the location where the laser beam energy should be applied. If either or both of these surface conditions for a particular wire changes, such as a gap between the wire end and the shoulder, the position of the laser beam needs to compensate for the gap for an optimal weld to be produced. It is very difficult to quantify all the surface conditions that exist for each wire to be welded. With so many position variables, it is difficult to make weld joints with consistent performance.

In many cases, the connector is used as a transition from a coil to another coil. The design of connectors requires the preparation and assembly of one coil onto the connector followed by the preparation and assembly of the other coil to the same connector. This is a time-consuming process that does not lend itself to fabrication of subassemblies for use in an efficient manufacturing flow.

Typical of the prior art relating to joints between windings and connectors is U.S. Pat. No. 4,953,564 which discloses a cardiac pacing lead having an extendible fixation helix electrode that is mechanically and electrically connected to a rotatable conductor coil by squeezing the helix and coil together between a crimping sleeve and a crimping core. As the sizes of body implantable leads and their constituent parts become smaller, crimping becomes more difficult because the crimping tools cannot be made sufficiently small. Moreover, the same number of lead windings are not always subjected to the crimping action so that failure stress differs from lead to lead.

Some other selective examples of the patented prior art which can be mentioned briefly include U.S. Pat. No. 5,569,883 to Walter et al. which discloses laser welding a wire coil to an intermediate ring or the like. U.S. Pat. No. 5,571,146 to Jones et al. discloses laser welding dissimilar materials by means of an aperture within a lead. U.S. Pat. No. 5,385,578 to Bush et al. discloses laser welding a wire coil to a sleeve.

It was with knowledge of the foregoing state of the technology that the present invention has been conceived and is now reduced to practice.

SUMMARY OF THE INVENTION

The invention comprises a laser weld joint according to which a lead winding is first joined to a ring which acts as a transition to a connector in order to achieve an optimal weld. The parts may be of dissimilar or similar materials. With the use of the transition ring, it is not necessary to depend upon the operator or the laser beam to properly distribute an unequal amount of energy to the components, but rather it compensates for the required unbalanced application of energy. It allows the line operator to easily locate the beam to a clear position defined by a feature of a component where the energy delivered will create a solid weld because the energy delivered was "balanced." The transition ring is butted against the prepared terminal end of the wound element and suitably held in compression by tooling. The coil is not expanded over or onto the transition ring or the connector. This requires one less manufacturing operation and allows the overall product size to remain small. Moreover, the transition ring is assembled to the coil in a subassembly operation where all the wire preparation and other labor intensive operations occur. This is valuable because now the subassembly may be assembled easily to the rest of the product. If it is joined to the product by another weld, the transition ring would also be designed to balance the energy required for the weld to the connector itself. Thus, the transition ring optimizes the manufacturability and reliability of the welded joint between the winding and the connector.

The proposed design is a winding and a transition ring subassembly. The subassembly will be welded to the connector. The ring and the winding have same inner and outer diameter. The ring sits against end of the winding. The wire ends (the very last wind) are welded to the transition ring, using a circumferential or spot laser. The transition ring/winding subassembly is then welded to the connector. The transition ring dimensions are specifically chosen to simulate an equal laser beam energy distribution between the wires and the transition ring. The outer diameter of the transition ring and connector can be reduced to outer diameter of winding. Once welded, a reliable joint is created because of positive weld reinforcement. Because the energy is balanced, a significant amount of the transition ring melts; and thus, adding material to the joint resulting in positive weld reinforcement. Moreover, after welding and adding material to joint from the transition ring, the weld joint has an outer diameter less than that of current designs. The decrease in diameter results in smaller products available in the marketplace.

This subassembly is then welded to the main assembly with minimal cost in terms of time, because all subassembly operation (wire trimming and positioning) have already been completed. Now a weld more suitable for joining the ring to the connector may be completed. The transition ring is capable of addressing the energy balance for two weld joints (wire to ring and ring to connector). The results shows that the two welds are designed specifically to take advantage of the positive time/cost reductions and reliability improvements that the individual welds provide.

For the best results the ring profile could be to provide some additional melted metal to create the weld positive reinforcement which increases strength and reliability of the product (see FIG. 5).

A primary feature, then, of the present invention is the provision of a significantly improved technique for providing a secure electrical and mechanical connection between wound elements, such as coil conductors, and mating parts such as electrodes, sensors and the like, employed within such lead assemblies.

Another feature of the present invention is the provision of such a technique employing a laser.

Still another feature of the present invention is the provision of such a technique which can achieve a satisfactory connection whether or not the alloys of which the components are fabricated are the same or dissimilar.

Still another feature of the present invention is the provision of such a technique which includes targeting a laser beam on a ring member and an adjoining end portion of the wound element and thermally fusing the two components together.

Yet another feature of the present invention is the provision of such a technique in which the geometry of the transition ring design allows the one or more weld joints to be formed from equal amounts of material from each part joined. The result of equal amounts of material comprising the joint is a process which attains the optimal strength of the joint in a consistent and repeatable manner.

Yet a further feature of the present invention is the provision of such a technique in which the joint configuration, namely, the winding to the transition ring, allows laser beam energy balance. The laser beam is targeted right on the middle of the joint located between wire ends and the edge of the ring. This increases the manufacturability and reliability of the joint. Location of where the laser energy should be delivered is easy for an operator to perform and the accuracy of locating the beam required for an acceptable joint is decreased. The laser beam is no longer used to determine the amount of energy delivered to the individual components.

Still a further feature of the present invention is the provision of such a technique according to which the design of the transition ring does not require expansion of the coil over or onto the ring. It maintains the original size of the coil. After welding, the proposed joint has an outer diameter less than that of current designs. The smaller diameter of the joint directly results in a smaller finished product.

Another feature of the present invention is the provision of such a technique according to which optimal weld joint strength is achievable because the design of the weld joint is no longer sensitive to the position of the wire ends with respect to the connector. The design of the weld joint is robust enough to compensate for the position of the wire ends. Moreover, the transition ring design decreases the number of degrees of freedom for error to occur by requiring the wire to work with only one surface.

Yet another feature of the present invention is the provision of such a technique according to which a winding with transition rings can be used as subassembly components on a production line. The transition ring is capable of addressing the energy balance for two weld joints, that is, wire to ring and ring to connector. It takes advantage of the positive time/cost reductions and reliability improvements that the individual welds provide.

Still a further feature of the present invention is the provision of such a technique according to which winding ring and connector can be made from the same or different materials.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

DETAILED DESCRIPTION OF THE PREFERRED EMBODIMENTS

Of primary concern with laser welding of two metals is that there must exist a balance between energy to be delivered to the metal masses. Known connections between lead wire ends (usually a multifilar winding) to the shoulder of an electrode mount or connector is a circumferential weld. The problem with this type of weld is that the laser beam must heat a large mass of connector in order to obtain a satisfactory melt to heat and cause fixation of the wire ends. This technique is time-consuming, has a tendency of overheating of the components being joined, particularly the wire winding, and has inconsistent results (i.e., reliability defects).

Alternately, spot welding has the advantages of less concern for overheating. However, current techniques of spot welding (for example, a weld on each wire end) have had inconsistent results. Filars do not always line up appropriately and/or don't get welded consistently. Disadvantages of this technique include misbalancing of energy; also, it is time-consuming to target the energy beam at the exact locations needed.

Each of these techniques has been implemented with such inconsistent results, that throughput in production varies greatly. What is needed is a high reliability weld connection with increased manufacturability, that is, repeatability and reduced assembly time. These benefits are provided by the present invention.

Figure 1:
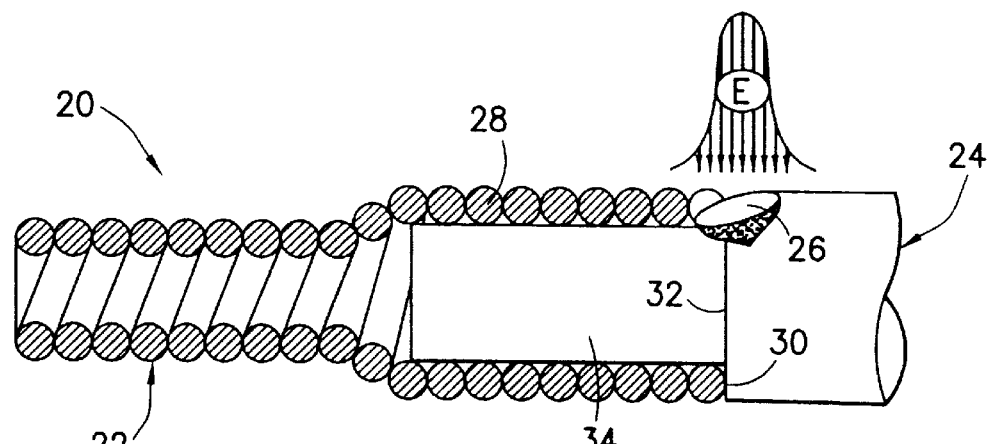
FIG. 1 is a diagrammatic side elevation view of a known laser weld assembly between a multi wire winding and a connector.

Turn now to the drawings and, initially, to FIG. 1 which generally illustrates a conventional circumferential laser weld assembly 20 between a multi wire winding 22 and a connector 24. To achieve this weld assembly 20, weld spots 26 obtained by use of a laser represented by a beam E, should be distributed around the periphery of the connector to melt together each wire strand 28 and the connector 24 itself. The common weld assembly comprises the winding 22 screwed or otherwise applied onto the cylindrical connector 24. The very last wind (wire ends 30) butts up against a shoulder 32 of the connector. The shoulder 32 and the last wind (wire ends 30) are thereby welded together.

As earlier explained, the connector 24 requires more laser energy to melt than does the wire strand 28 and the weld region needs more melted metal to increase strength of the weld assembly. During welding, the laser beam E melts both the connector 24 and the winding 22. The wire possesses less metal mass than does the connector. As such, the winding accumulates heat very quickly and the wire strands 28 can melt easily. The melted metal from the winding spreads over the connector forming the weld spot 26. A lack of melted metal creates wire "neck down" and negative weld reinforcement, which reduces the strength of weld joint. The connector has much more metal mass, which means it draws the heat out of the weld area. Unfortunately, this condition makes it difficult to melt the metal to fuse the components together. Therefore, the connector requires more energy from the laser beam E to melt than does the winding. To achieve a reliable weld, the beam energy must be specifically balanced between the connector and the winding. The proper beam targeting requires placement of the laser beam unequally on the joint such that more energy is on the shoulder side than on the wire. However, it is difficult for the assembly line operator to properly target the laser beam on the joint. A difference in material thermal properties further magnifies the energy balance problem. For example, platinum requires much more energy to melt than does MP35N, a high corrosion resistant stainless steel used for implantable devices including leads. If a joint comprises MP35N wire and a platinum connector it will need a greater misbalance of energy to melt the components equally. Proper beam targeting required to achieve a solid weld becomes more critical with dissimilar materials than with similar materials.

Figure 2:
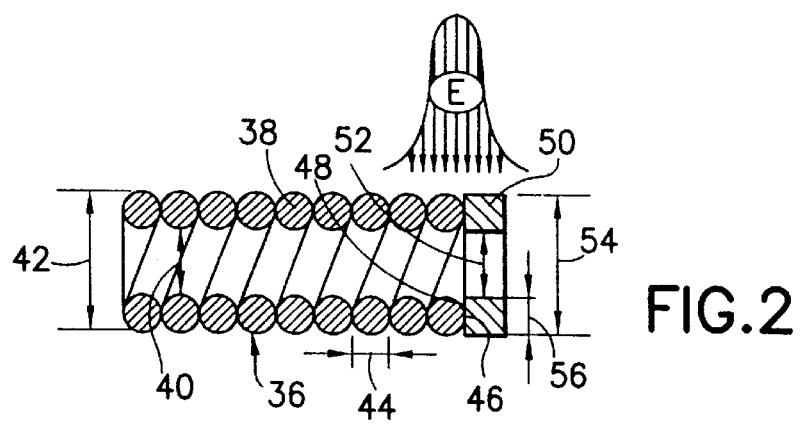
FIG. 2 is a diagrammatic side elevation view, similar to FIG. 1 but illustrating one step of a laser weld assembly operation embodying the invention utilizing a transition component.
Figure 3:
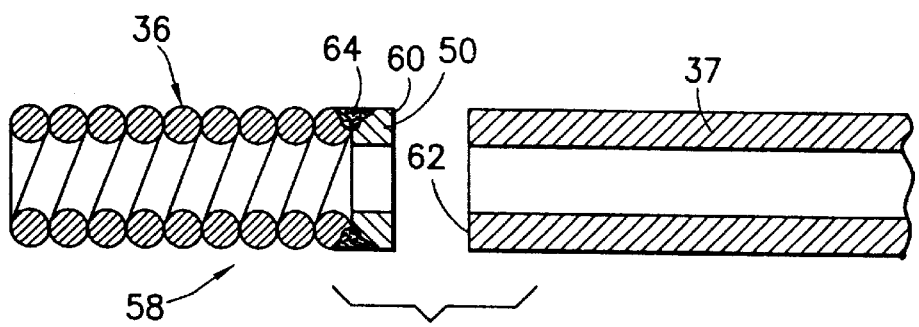
FIG 3 is a diagrammatic side elevation view illustrating the alignment of a winding subassembly resulting from the operation illustrated in FIG. 2 and a mating connector to which the subassembly is to be joined.

For a description of the present invention, turn now to FIGS. 2 and 3. However, return momentarily to the joint illustrated in FIG. 1 which requires the wire strand 28 to be screwed onto a reduced diameter post projecting from the shoulder 32 of the connector 24. With this operation, it is seen that the diameter of the winding 22 is necessarily enlarged in order to be properly engaged with the post 34. In contrast, an elongated wound element 36 is joined to a mating connector 37 of a body implantable lead assembly without requiring any diameter enlargement of the wound element. As seen in FIG. 2, the wound element 36 is a coiled wire strand 38 including at least one wire having an inner diameter 40 and an outer diameter 42 and the wire strand having a nominal diameter 44.

According to the invention, an end portion 46 of the wound element 36 is caused to abut against a first end 48 of a transition component 50 having mass and heat transmission characteristics which are similar to the wound element. Specifically, the transition component 50 is a ring member which has inner and outer diameters 52, 54 which are substantially the same, dimensionally, as the coiled wire strand 38 and a transverse dimension 56 similar to the nominal diameter of the wire strand.

Thereupon, the end portion 46 of the wound element 36 is joined to the first end 48 of the transition component to form a winding subassembly 58 (FIG. 3). This is achieved by thermally fusing the end portion of the wound element 36 and the first end 48 of the transition component 50, preferably by targeting a laser beam E generally at the location at which the end portion of the wound element abuts against the end of the transition component such that the energy delivered thereto is substantially balanced between the wound element and the transition component. Thereafter, with the transition component 50 now integral with the wound element 36, a second end 60 of the transition component distant from the first end 48 is caused to abut against an end portion 62 of the mating connector 37. At this point, the second end 60 of the transition component 50 and the end portion 62 of the mating connector 37 are joined together by a thermal fusing process, again preferably by targeting the laser beam E generally at the location at which the end portions 60, 62 abut and such that the energy delivered thereto is substantially balanced between the two components.

Figure 4:
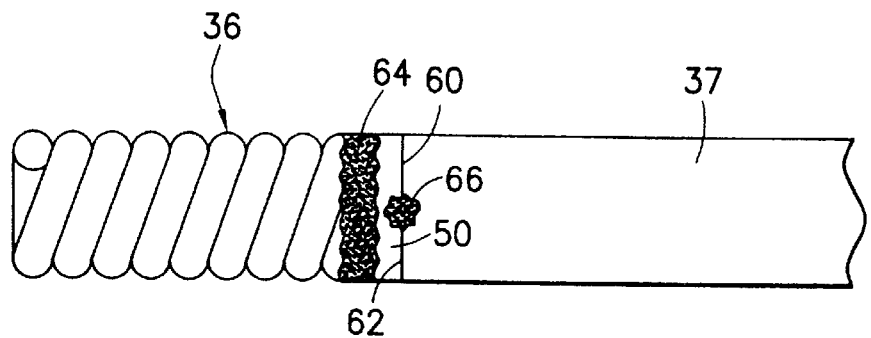
FIG. 4 is a diagrammatic side elevation view illustrating the winding subassembly joined with the mating connector.

While, as seen in FIG. 4, it may be desirable for the weld joint 64 between the wound element 36 and the transition component 50 to be a continuous circumferential weld, discontinuous spot welds may also be used. Similarly, the joint between the transition component and the mating connector 37 may be properly achieved either by a continuous circumferential weld or by two or more circumferentially spaced spot welds 66.

It will be appreciated that the resulting joint illustrated in FIG. 4 is achieved regardless of whether the wound element and the transition component are fabricated of the same alloy or of dissimilar alloys.

Figure 5:
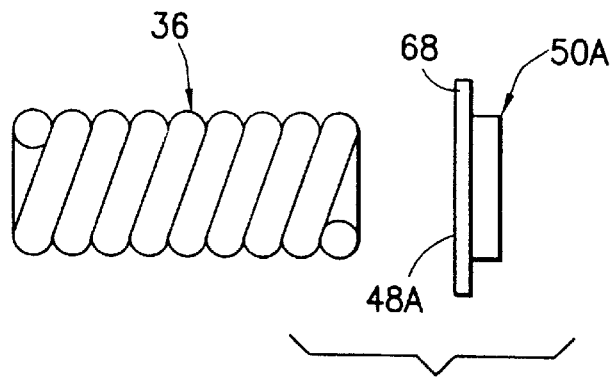
FIG. 5 is a diagrammatic side elevation view, exploded, illustrating another construction of the winding subassembly utilizing a modified transition component.
Figure 6:
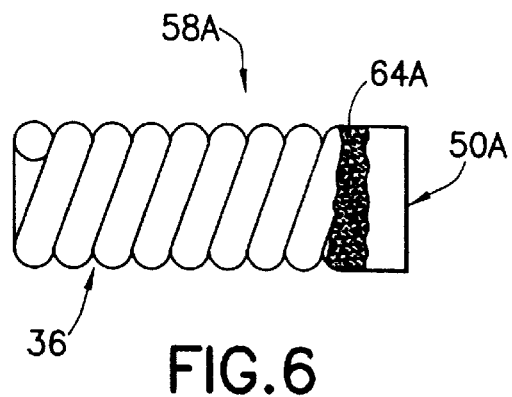
FIG. 6 a diagrammatic side elevation view illustrating the modified joined winding subassembly utilizing the modified transition component.

Turning now to FIGS. 5 and 6, another embodiment of the invention is illustrated wherein a modified transition component 50A is a ring member which has inner and outer diameters, as with the transition component 50, which are substantially the same as those dimensions of the wound element, the ring member also having a thickness which is substantially similar to the nominal diameter of the wire of the coil of at least one wire. However, in this instance, the ring member has an annular flange 68 adjacent a first end 48A and the annular flange is reduced in diameter substantially to the outer diameter of the wound element 36 and of the mating connector upon completion of the thermal fusing operation resulting in the weld joint 64A. The benefit thereby achieved is that, during the welding process, the annular flange 68 provides an additional amount of melted metal to cover the end portion of the wound element 36, filling the gaps between the wire segments and between the wire segments and the transition component 50A and producing positive weld reinforcement.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. A joint connecting an elongated wound element and a mating connector of a body implantable lead assembly comprising:

a transition component having first and second spaced apart ends and mass and heat transmission characteristics which are similar to the wound element;

an end portion of the wound element being abutted against the first end of the transition component and being integrally joined to the transition component by mutual melting of the wound element and of the transition component and the resulting thermal fusion of the wound element and of the transition component; and the second end of the transition component being abutted against an end portion of the mating connector and being integrally joined to the mating connector by mutual melting of the transition component and of the mating connector and the resulting thermal fusion of the transition component and of the mating connector.

2. The joint as set forth in claim 1, wherein the wound element and the transition component are fabricated of the same alloy.

3. The joint, as set forth in claim 1, wherein the wound element and the transition component are fabricated of dissimilar alloys.

4. The joint, as set forth in claim 1, wherein the wound element is a coil of wire defining plural wire segments, and wherein the transition component is a ring member which has inner and outer diameters which are substantially the same as those dimensions of the coil of wire, the ring member having a thickness which is substantially similar to the nominal diameter of the wire of the coil of at least one wire, the ring member having an annular flange adjacent the first end, the annular flange being reduced in diameter substantially to the outer diameter of the wound element and of the mating connector upon completion of thermal fusion of the transition component and of the mating connector, the annular flange thereby providing an additional amount of melted metal to cover the end portion of the wound element, filling any gaps existing between the wire segments and between the wire segments and the transition component and producing positive weld reinforcement.

* * * * *